United States Patent
Wang

(10) Patent No.: US 10,722,563 B2
(45) Date of Patent: Jul. 28, 2020

(54) PROSTATE-SPECIFIC TUMOR ANTIGENS AND USES THEREOF

(71) Applicant: SHENZHEN INNOVATION IMMUNOTECHNOLOGY CO., LTD., Shenzhen (CN)

(72) Inventor: Rongfu Wang, Houston, TX (US)

(73) Assignee: SHENZHEN INNOVATION IMMUNOTECHNOLOGY CO., LTD., Shenzhen (CN)

( * ) Notice: Subject to any disclaimer, the term of this patent is extended or adjusted under 35 U.S.C. 154(b) by 667 days.

(21) Appl. No.: 14/663,470

(22) Filed: Mar. 20, 2015

(65) Prior Publication Data

US 2015/0202273 A1 Jul. 23, 2015

Related U.S. Application Data

(63) Continuation-in-part of application No. PCT/US2013/060254, filed on Sep. 18, 2013.

(60) Provisional application No. 61/703,761, filed on Sep. 20, 2012.

(51) Int. Cl.
*A61K 39/00* (2006.01)
*A61K 38/19* (2006.01)
*A61K 45/06* (2006.01)

(52) U.S. Cl.
CPC ........ *A61K 39/0011* (2013.01); *A61K 38/193* (2013.01); *A61K 45/06* (2013.01)

(58) Field of Classification Search
None
See application file for complete search history.

(56) References Cited

U.S. PATENT DOCUMENTS

2003/0091562 A1* 5/2003 Jakobovits ............. C07K 14/47
424/142.1

FOREIGN PATENT DOCUMENTS

WO WO 02/092842 * 11/2002

OTHER PUBLICATIONS

Heidi L: Programs face off in cancer contest. Nature, vol. 540, Dec. 15, 2016 (328-329).

* cited by examiner

*Primary Examiner* — Alana Harris Dent
(74) *Attorney, Agent, or Firm* — Duane Morris LLP; Thomas J. Kowalski; Deborah L Lu

(57) ABSTRACT

Twenty-one PSGR-derived peptides predicted by an immuno-informatics approach based on the HLA-A2 binding motif were examined for their ability to induce peptide-specific T cell responses in peripheral blood mononuclear cells (PBMCs) obtained from either HLA-A2+ healthy donors or HLA-A2+ prostate cancer patients. The recognition of HLA-A2 positive and PSGR expressing LNCaP cells was also tested. Three peptides, PSGR3, PSGR4 and PSGR14 frequently induced peptide-specific T cell responses in PBMCs from both healthy donors and prostate cancer patients, and are recognized by CD8+ T cells in an HLA-A2 dependent manner. These peptide-specific T cells recognize HLA-A2+ and PSGR+ tumor cells, and killed LNCaP prostate cancer cells in an HLA class I-restricted manner. These PSGR-derived peptides identified are useful as diagnostic markers as well as immune targets for anti-cancer vaccines.

5 Claims, 6 Drawing Sheets

Specification includes a Sequence Listing.

PROSTATE-SPECIFIC TUMOR ANTIGENS AND USES THEREOF

BACKGROUND OF THE INVENTION

Prostate cancer has become the most common cancer and is the second leading cause of death from cancer in American men [1]. The standard of care is surgery and/or radiation therapy. However, disease recurrence after surgery or radiation still takes place in up to 30% of patients. Although androgen-deprivation therapy is effective, most of these patients eventually develop androgen-refractory prostate cancer. Therefore, more effective and less toxic therapies are urgently needed.

Immunotherapy has been shown to be a promising approach to the treatment of prostate cancer, especially for patients with metastatic castration-resistant prostate cancer [2-4], but until recently it has been met with only sporadic clinical success [4-6]. Recent Food and Drug Administration (FDA) approvals of the immunotherapy-based vaccine/drug sipuleucel-T (Provenge) and ipilimumab (Yervoy) represent milestones in the field of cancer immunotherapy [7,8]. Furthermore, a phase III clinical trial of the gp100 peptide for melanoma also produced highly encouraging clinical results [9]. However, the clinical benefits reported for these agents have fallen far short of complete responses and permanent cures. In the case of sipuleucel-T, the survival benefit for patients was only 4.1 months, without objective tumor regression or substantial changes in prostate specific antigen (PSA) levels. A recent study using animal models further reveals the importance of tumor-specific antigens in eliciting immune responses against a developing tumor [10], spurring more efforts to identify such antigens for cancer immunotherapy. Furthermore, since some major rejection antigens may be lost or altered due to T cell selection and killing [11], the best strategy is to target multiple tumor antigens that are present on individual tumors for immunotherapy.

A number of prostate specific tumor antigens have been well-defined, including PSA [12,13], prostein [14,15], prostate stem cell antigen (PSCA) [16], prostate-specific membrane antigen (PSMA) [17-19], prostatic acid phosphatase (PAP) [20] and transient receptor potential p8 (trp-p8) [21]. Furthermore, HLA-class I-restricted epitopes derived from these tumor antigens have been described [22]. One drawback of single tumor antigen-based immunotherapy is that immune escape may occur. Hence, there is a need to identify additional prostate cancer-specific antigens for development of more effective and antigen-specific vaccines for metastatic prostate cancer.

SUMMARY OF THE INVENTION

Prostate-specific G-protein coupled receptor (PSGR) is a member of the G-protein coupled odorant receptor family, and is highly expressed in prostate cancer cells compared with normal prostate cells [23-25], suggesting that PSGR may be targeted for the development of novel immunotherapeutic strategies against prostate cancer.

We determined that PSGR is recognized by T cells, and describe PSGR-derived T cell epitopes for T cell recognition. Twenty-one peptides predicted to bind to the HLA-A2 molecule were selected and synthesized, and evaluated in vitro for their ability to stimulate T cells in PBMCs from both healthy subjects and prostate patients based on interferon-γ (IFN-γ) release measured by ELISA or ELISPOT assays. Three peptides, namely PSGR3, PSGR4 and PSGR14 (see below and Table 1) were found to induce IFN-γ release in peripheral T cells from both healthy subjects and prostate cancer patients. Importantly, these peptide-specific T cells could recognize HLA-A2$^+$, PSGR-expressing LNCaP cells in an HLA-class dependent manner.

Accordingly, the present invention provides, in one embodiment, a composition comprising a polypeptide consisting of the amino acid sequence of PSGR3, PSGR4 or PSGR14, or combinations of two or more of the three peptides, and a pharmaceutically acceptable carrier.

In one aspect the present disclosure provides a method of treating or preventing prostate cancer comprising administering to a patient in need thereof an effective amount of the composition of the present invention.

In an embodiment, the disclosure provides a method for treating prostate cancer in a human patient comprising the step of administering a composition of the disclosure to the patient in an amount effective to stabilize or reduce the level of serum prostate-specific antigens (PSA), in particular the PSGR level. In some aspects, methods of the disclosure further comprise administrating granulocyte monocyte colony stimulating factor (GM-CSF). In these aspects, the composition and GM-CSF are co-administered, and in further embodiments said composition and GM-CSF are administered concurrently while in still further embodiments said composition and GM-CSF are administered sequentially.

In some embodiments, the PSGR is administered as a composition of dendritic cells pulsed respectively with the PSGR peptide, for example in multiple injections.

Administration of a composition or vaccine of the disclosure may be, in various aspects, intradermal. Thus, the disclosure also provides a vaccine comprising: (i) a polypeptide consisting of the amino acid sequence of PSGR3, PSGR4 or PSGR14, or combinations of two or more of the three peptides, and (ii) a pharmaceutically acceptable carrier. In some aspects, the vaccine further comprises granulocyte monocyte colony stimulating factor (GM-CSF). In further aspects, the vaccine further comprises a toll-like receptor 9 (TLR9) agonist in an amount effective to increase a T cell immune response. In one specific aspect, the TLR9 agonist is a CpG-oligodeoxynucleotide (CpG-ODN).

In further embodiments, the vaccine further comprises an inhibitor of CTLA4 in an amount effective to increase a T cell immune response, and in a specific aspect the inhibitor of CTLA4 is a monoclonal antibody.

In additional embodiments, the vaccine further comprises an inhibitor of PD-1 in an amount effective to increase a T cell immune response. In a specific aspect, the inhibitor of PD-1 is a monoclonal antibody.

The disclosure also provides a method of vaccinating an individual comprising the step of administering a vaccine of the present invention to the individual in an amount effective to vaccinate the individual. In some aspects, the vaccine of the present invention is co-administered with GM-CSF, and in further aspects in multiple injections. In further aspects, the PSGR peptide(s) and GM-CSF are administered concurrently while in yet further aspects they GM-CSF are administered sequentially.

Figure 1:
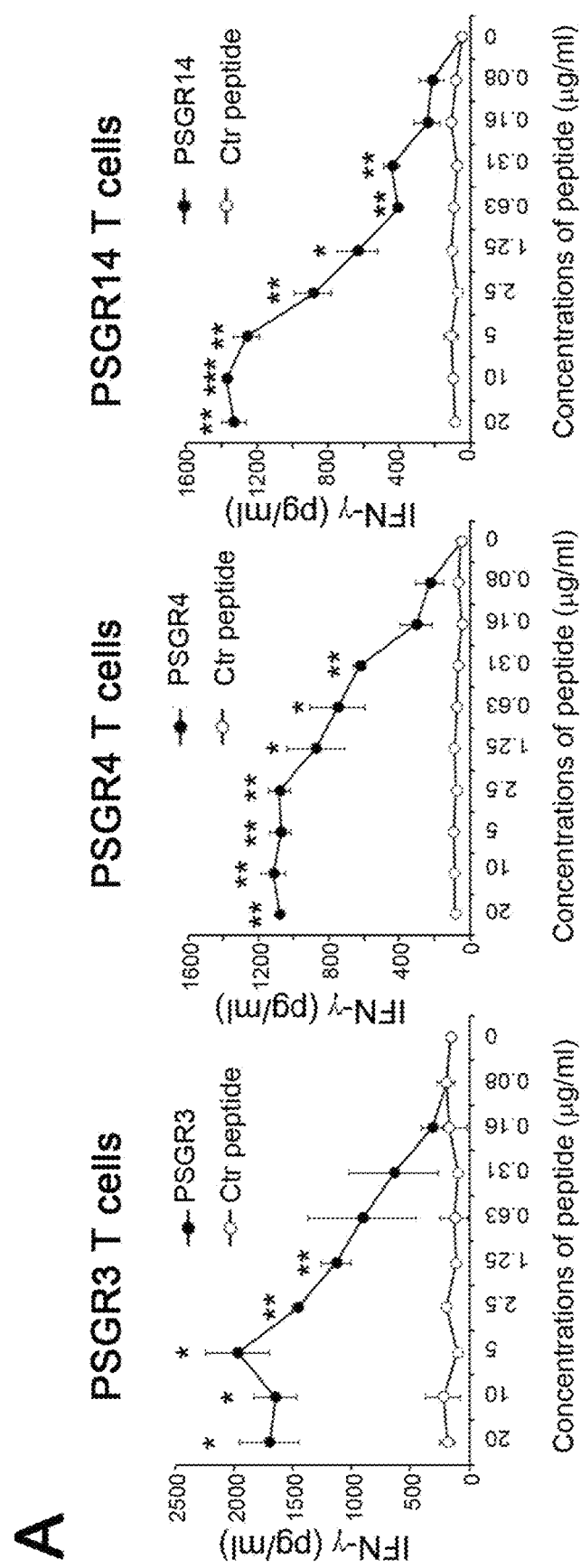
FIG. 1 shows that PSGR-derived peptides induced peptide-specific T cells. The recognition of T2 cells pre-loaded with titrated concentrations of peptides (0-20 μg/ml) by expanded PSGR peptide-specific T cells was tested by ELISA assay (A). The expanded PSGR3 T cells (B and E), PSGR4 T cells (C and F) and PSGR14 T cells (D and G) were respectively co-incubated with T2 cells (1×10⁴ cells/well) alone in complete medium (CM), or with T2 cells pre-loaded with either a corresponding peptide (5 μg/mL) or a control peptide as a negative control. Cells were incubated for 18-24 hours, the IFN-γ secretion in the supernatant was determined by ELISA assay (B, C and D). IFN-γ spot-forming cells (SFC) were enumerated by ELISPOT assay (E, F and G). Data are plotted as means±SD. Results are representative of at least three independent experiments. *P <0.05, P<0.01, * P<0.001 versus controls (T2 cells alone or T2 cells pulsed with a control peptide).
Figure 1:
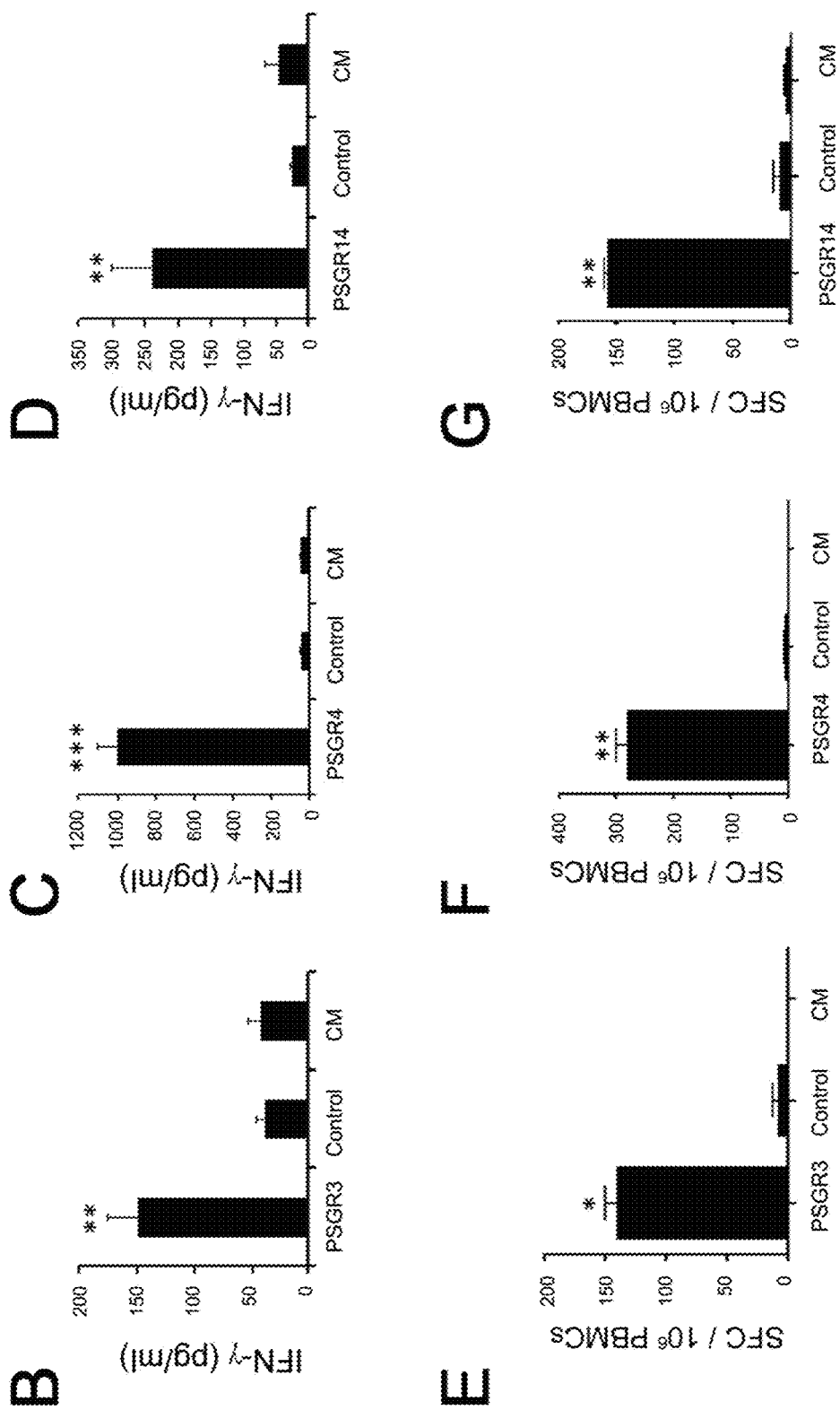

DESCRIPTION OF THE INVENTION it is well established that CD8⁺ T cells play a critical role in controlling tumor development and progression. Peptide epitopes derived from tumor-associated antigens (TAAs) can be recognized as antigens by T cells in the context of MHC-I molecules [32,33]. Identification of TAAs and their peptides that are recognized by T cells are essential for the development of effective cancer vaccines.

We set out to identify human leukocyte antigen A2 (HLA-A2) binding PSGR-derived epitopes recognized by CD8⁺ T cells in PBMCs of healthy subjects and prostate cancer patients. Three different computer-based prediction algorithms including BIMAS, SYFPEITHI, and Rankpep were used to scan the PSGR protein sequence for HLA-A2 binding peptides based on the HLA-A2 binding motif. Only peptides that were predicted successfully by at least 2 out of 3 of the different computer-based prediction algorithms were included. Twenty-one 9mer or 10mer peptides were selected in this study according to this criterion. All these peptides were tested for their ability to stimulate PBMCs from either healthy subjects or prostate cancer patients to release IFN-γ. Of 21 peptides, three peptides frequently induced specific T cell responses in PBMCs obtained from either healthy subjects or cancer patients, and these peptide-specific T cells also recognized HLA-A2⁺ PSGR-expressing LNCaP cells, suggesting that these peptides are naturally processed by prostate cancer cells.

PSGR is a prostate tissue-specific gene with homology to the G protein-coupled odorant receptor gene family and it is specifically expressed in human prostate tissues [23-25]. The expression of PSGR is significantly higher in human prostate intraepithelial neoplasia and prostate tumors than normal tissues [25]. Intriguingly, although PSGR has been considered to be a novel target for prostate cancer immunotherapy, T cell epitopes derived from PSGR have not been identified. This is, to our knowledge, the first report to identify and characterize PSGR-derived epitopes recognized by CD8⁺ T cells. The identification of PSGR-derived epitopes recognized by T cells further validates PSGR as a promising target for the development of cancer vaccines.

Most TAAs are self-antigens [34], therefore, self-tolerance may occur in an attempt to protect the individual from the development of autoimmunity. This is considered to be a major obstacle in the induction of TAA-specific T cells capable of eradicating tumors in vivo. However, in our study, although PSGR is expressed in normal prostate tissue, immune tolerance against PSGR can be broken, since T cell responses against PSGR-derived epitopes were frequently detectable in PBMCs from either healthy subjects or prostate cancer patients.

A vast number of immunotherapy clinical trials based on vaccinations with tumor lysates, TAA proteins, TAA peptides and RNA or DNA encoding TAA have already been conducted. However, most of these trials have not achieved desirable results. One reason is that expression of these TAAs is heterogeneous among tumors from different patients and can vary even among metastases obtained from one patient [35,36], thus immune escape may occur when the immunotherapeutic approach is only based on one TAA. To avoid immune escape, vaccine-based immunotherapeutic strategies that target several tumor antigens are essential for the development of successful cancer vaccines. Thus identification of additional prostate specific tumor antigens, such as PSGR, for T-cell-based immunotherapy is still needed, despite that a number of prostate specific tumor antigens including PSA [12,13], PSCA [16], PSMA [17-19], PAP [20], Prostein [14,15] and trp-p8 [21], have been identified in the last few years.

The FDA has recently approved a cancer vaccine, Sipuleucel-T, for the treatment of patients with advanced prostate cancer based on a phase III study [8]. Sipuleucel-T is prepared from autologous PBMCs containing antigen presenting cells that are incubated with a recombinant protein composed of a PAP linked to granulocyte-macrophage colony-stimulating factor (GM-CSF). Sipuleucel-T presumably works in part by augmenting PAP-specific CD8+ T cell responses, further demonstrating the importance of tumor antigen-specific CD8+ T cells induced by cancer vaccines. So far, Sipuleucel-T is the first cellular immunotherapeutic agent approved by the FDA to be used for the treatment of cancer patients. The FDA approval of Sipuleucel-T as a therapeutic cancer vaccine not only validates the efficacy of cancer immunotherapy, but also provides a strong impetus in the field of cancer immunology [37]. Therefore, identification and development of more novel TAAs including PSGR and peptide derivates recognized by CTLs is definitely essential to facilitate the development of effective cancer vaccines against prostate cancers as well as other types of cancers in the future.

Furthermore, the epitopes recognized by CD8+ T cells may be used as diagnostic tools to monitor peptide-specific CD8+ T cells in individuals during the course of immunization, thus identifying optimal time frames for immunization during treatment, including whether subsequent immunizations are needed in individuals when anti-tumor immunity declines.

The PSGR derived peptide of the present invention can also be attached to a non-polypeptide molecule for the purpose of conferring desired properties such as reducing degradation and/or increasing half-life, reducing toxicity, reducing immunogenicity, and/or increasing the biological activity. Exemplary molecules include but are not limited to linear polymers such as polyethylene glycol (PEG), polylysine, a dextran; a lipid; a cholesterol group (such as a steroid); a carbohydrate, or an oligosaccharide molecule.

In one embodiment, the amino acid sequences of the PSGR derived peptide of the present invention are shown in Table 1. In one embodiment, the PSGR derived peptide comprises a polypeptide having the sequence set forth in SEQ ID NOs: 3, 4, or 14. In another embodiment, the polypeptide has an amino acid sequence with at least 80%, 85%, 90%, 95%, 98% or 99% identity to the polypeptides above, wherein the polypeptide is capable of inducing peptide-specific T cells which recognize HLA-A2 positive PSGR-expressing prostate cancer cells. Preferably, these T cells are cytotoxic to the cancer cells. Preferably, the polypeptides are able to induce T cell responses (such as peptide-specific cytotoxic T lymphocytes (TCLs) from PBMCs of prostate cancer patients), which preferably are CD8+ T cell dependent and restricted by HLA-I.

Compositions of the present invention comprise a therapeutically or prophylactically effective amount of the polypeptide or protein in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents: excipients and/or pharmaceutical adjuvants. (Remington's Pharmaceutical Sciences, 18$^{th}$ Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffers, or acetate buffers, which may further include sorbitol or a suitable substitute thereof. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly (2-hydroxyethyl-methacrylate) (Langer et al., J. Biomed. Mater. Res., 15:167-277, (1981); Langer et al., Chem. Tech., 12:98-105 (1982)), ethylene vinyl acetate (Langer et al., supra) or poly-D(–)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein/peptide and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, the PSGR derived peptide of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the polypeptide product(s) but prevent the destruction of the cells by the patient's immune system or by other detrimental factors from the surrounding tissues.

A gene therapy in vivo is also envisioned wherein a nucleic acid molecule encoding the PSGR derived peptide of the present invention, or a derivative thereof is introduced directly into the subject. For example, a nucleic acid sequence encoding a PSGR derived peptide of the present invention is introduced into target cells via local injection of a nucleic acid construct with or without an appropriate delivery vector, such as an adeno-associated virus vector. Alternative viral vectors include, but are not limited to, retroviruses, adenovirus, herpes simplex virus and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

The compositions of the present disclosure may be used alone or in combination with other therapeutic agents to enhance their therapeutic effects or decrease potential side effects.

Another object of the present invention is to provide methods preparing the above PSGR derived peptide and the pharmaceutical composition comprising it. In one embodiment, the preparation method comprises the steps of: (1) providing an encoding polynucleotide molecule; (2) constructing an expression vector comprising the polynucleotide molecule of (1); (3) transfecting or transforming suitable host cells with the expression vector in (2) and cultivating to express the protein in the host cells; and (4) purifying the protein. The preparation may be carried out with proven and well-known technologies by an ordinarily skilled artisan.

Another object of the present invention is to provide method of treating cancer using the pharmaceutical composition of the present invention comprising administrating an effective amount of the aforementioned pharmaceutical composition to the patients or subjects in need thereof.

Also, the present invention provides a polynucleotide molecule encoding the PSGR derived peptide and an expression vector expressing the PSGR derived peptide. Examples of vectors include but are not limited to plasmic's, viral vectors, yeast artificial chromosomes (YACs), bacterial artificial chromosomes (BACs), transformation-competent artificial chromosomes (TACs), mammalian artificial chromosomes (MACs) and human artificial episomal chromosomes (HAECs).

The present invention provides host cells comprising the above expression vectors. The host cells may be transformed or transfected with the expression vectors. Suitable host cells include prokaryocytes, yeasts and other eukaryotes. Preferably, *Escherichia coli*, yeast or mammalian cell lines (such as COS or CHO) are used.

In summary, we have identified three novel PSGR-derived CTL epitopes. Since PSGR expression is strongly up-regulated in human prostate cancers, PSGR-derived peptides may serve as diagnostic tools or immunotherapeutic targets of anticancer vaccines alone or in combination with other epitopes that are derived from other prostate-specific antigens.

The invention is illustrated by the following examples, which are not intended to be limiting in any way.

EXAMPLES

Materials and Methods

Healthy Donors and Prostate Cancer Patients

Ten HLA-A2+ prostate cancer patients and ten HLA-A2+ healthy subjects were enrolled in this study after written informed consent was obtained. All protocols were approved by the Institutional Review Board (IRB) of Baylor College of Medicine before commencing studies. 20 mL of peripheral blood was obtained from each person, and peripheral blood mononuclear cells (PBMCs) were isolated by density gradient centrifugation using Lymphoprep (Nycomed Pharma AS; Oslo, Norway). The freshly isolated PBMCs were cryopreserved for later use in 1 mL freezing medium containing 90% FCS and 10% dimethyl sulfoxide (DMSO) at −140° C. The expression of HLA-A2 molecules on PBMCs obtained from cancer patients and healthy subjects was verified by flow cytometry with FITC-labeled HLA-A2 mAb BB7.2 (BD Pharmingen, San Diego, Calif., USA).

Cell Lines

T2 cells (an HLA-A2+ TAP-deficient cell line), PC3 cells (an HLA-A2-negative prostate cancer cell line), and LNCaP cells (an HLA-A2 positive prostate carcinoma cell line) were all purchased from American Type Culture Collection (ATCC; Manassas, Va., USA). All cell lines were maintained in RPMI-1640 medium (Mediatech; Manassas, Va., USA), supplemented with 10% FBS, 1% L-glutamine, and 1% penicillin and streptomycin.

Peptides

Twenty-one PSGR-derived peptides (Table 1) were predicted using BIMAS (www-bimas.cit.nih.gov/molbio/hla_bind/), SYFPEITHI (www.syfpeithi.de/), and Rankpep (bio.dfci.harvard.edu/Tools/rankpep.html) based on the HLA A2 binding motif. Only epitopes that were predicted by at least two of these algorithms were selected for further testing. The peptides were synthesized by a solid-phase method using a peptide synthesizer (AApptec, Inc.; Louisville, Ky., USA), purified by reverse-phase high-performance liquid chromatography and validated by mass spectrometry. The synthesized peptides were dissolved in DMSO at a concentration of 10 mg/mL and stored at −80° C. until further use.

TABLE 1 predicted HLA-A2 binding peptides derived from prostate-specific PSGR

| Peptide # | HLA restriction | Position | Sequence |
|---|---|---|---|
| PSGR1  | HLA-A2 | 287-295 | VLNPIVYGV (SEQ ID NO: 1) |
| PSGR2  | HLA-A2 | 188-196 | KLACDDIRV (SEQ ID NO: 2) |
| PSGR3  | HLA-A2 | 276-284 | ILANIYLLV (SEQ ID NO: 3) |
| PSGR4  | HLA-A2 | 28-36   | WLAFPLCSL (SEQ ID NO: 4) |
| PSGR5  | HLA-A2 | 220-228 | YLLILKTVL (SEQ ID NO: 5) |
| PSGR7  | HLA-A2 | 181-189 | CLHQDVMKL (SEQ ID NO: 6) |
| PSGR10 | HLA-A2 | 213-222 | SLLISFSYLL (SEQ ID NO: 7) |
| PSGR11 | HLA-A2 | 245-254 | HVCAVFIFYV (SEQ ID NO: 8) |
| PSGR12 | HLA-A2 | 21-30   | GLEEAQFWLA (SEQ ID NO: 9) |
| PSGR13 | HLA-A2 | 156-165 | ALMAPLPVFI (SEQ ID NO: 10) |
| PSGR14 | HLA-A2 | 275-284 | VILANIYLLV (SEQ ID NO: 11) |
| PSGR15 | HLA-A2 | 221-230 | LLILKTVLGL (SEQ ID NO: 12) |
| PSGR16 | HLA-A2 | 37-46   | YLIAVLGNLT (SEQ ID NO: 13) |
| PSGR17 | HLA-A2 | 66-75   | CMLSGIDILI (SEQ ID NO: 14) |
| PSGR18 | HLA-A2 | 100-109 | LLQMFAIHSL (SEQ ID NO: 15) |
| PSGR19 | HLA-A2 | 56-65   | SLHEPMYIFL (SEQ ID NO: 16) |
| PSGR20 | HLA-A2 | 117-126 | LLAMAFDRYV (SEQ ID NO: 17) |
| PSGR21 | HLA-A2 | 41-50   | VLGNLTIIYI (SEQ ID NO: 18) |
| PSGR22 | HLA-A2 | 250-259 | FIFYVPFIGL (SEQ ID NO: 19) |
| PSGR23 | HLA-A2 | 139-148 | TLPRVTKIGV (SEQ ID NO: 20) |
| PSGR24 | HLA-A2 | 253-262 | YVPFIGLSMV (SEQ ID NO: 21) |

In Vitro Stimulation of Peptide-Specific T Cells in PBMCs

PBMCs (1×105 cells/well) from either healthy subjects or prostate cancer patients were incubated with standard peptide concentrations of 20 µg/mL per peptide [26-28] in 96-well U-bottom microplates (BD, Franklin Lakes, N.J., USA) in 200 µL of T-cell medium (TCM), consisting of RPMI 1640 (Mediatech, Manassas, Va., USA), 10% human AB serum (Valley Biomedical, Winchester, USA), 50 µM of 2-mercaptoethanol, 100 U/mL of interleukin-2 (IL-2), and 0.1 mM MEM nonessential amino acid solution (Invitrogen, Grand Island, N.Y., USA). Half of the TCM was removed and replaced with fresh TCM containing peptides (20 µg/mL) every 5 days. After 14 days of culture, the cells were harvested and tested for their ability to produce IFN-γ in response to T2 cells (1×104 cells/well), which were preloaded with either PSGR peptide (5 µg/mL) or a control peptide (an irrelevant HL-A2 binding peptide: NLLTHVESL) as a negative control. After 18 hours of incubation, supernatants were collected, and IFN-γ release was determined by ELISA assay.

Rapid Expansion Protocol (REP) for PSGR Peptide-Specific

PSGR peptide specific T cells were expanded by a rapid expansion protocol (REP) as previously described [29] with a slight modification. Briefly, on day 0, 0.1-0.5×106 PSGR peptide specific T cells were cultured in a T25 flask with 20 mL RPMI-1640 supplemented with 10% human AB serum. 50 µM of 2-mercaptoethanol, and 30 ng/mL OKT3 antibody (Ortho Biotech, Bridgewater, N.J.), together with 20×106 irradiated allogeneic PBMCs and 5×106 irradiated Epstein Barr Virus (EBV) transformed B-cells as feeder cells. Flasks were incubated upright at 37° C. in 5% CO2. IL-2 (300 IU/mL) was added on day 1, and on day 5, half of the cell culture supernatant was removed and replenished with fresh medium containing 300 IU/mL IL-2. 14 days after initiation of the REP, cells were harvested and cryopreserved for future experiments.

ELISA Assay

Cytokine release was measured by coating 96-well ELISA plates (Thermo Fisher Scientific; Rochester, N.Y., USA) with 1 µg/mL anti-human IFN-γ (Pierce Biotechnology; Rockford, Ill., USA) overnight at 4° C. The plate was washed six times with PBS containing 0.05% Tween-20 (wash solution) to remove unbound coating antibody, and blocked with 1% BSA/PBS at room temperature for 2 hrs. Afterwards, 50 µL supernatant was added to each well and incubated at room temperature for 1 hr, then 50 µL of 0.5 µg/mL biotinylated anti-human IFN-γ (Pierce Biotechnology; Rockford, Ill., USA) was added and plates were incubated for an additional 1 hr at room temperature. After incubation, plates were washed and incubated for 30 min with Poly-HRP-Streptavidin (Thermo Fisher Scientific; Rochester, N.Y., USA) diluted 1:5000 in PBS/1% BSA. Plates were washed and 100 µL of TMB substrate solution (Sigma-Aldrich Co.; St. Louis, Mo., USA) was added per well. The colorimetric reaction was stopped using 2N H2SO4 and plates were read at 450 nm using an ELISA plate reader.

IFN-γ ELISPOT Assay

The IFN-γ ELISPOT assay was performed as previously described [27] to quantify peptide-specific cytotoxic T-lymphocytes (CTLs) after in vitro expansion. Briefly, 96-well ELISPOT plates (Millipore; Bedford, Mass., USA) were coated overnight at 4° C. with 7.5 µg/mL anti-human IFN-γ (Pierce Biotechnology; Rockford, Ill., USA). Plates were washed six times with sterile PBS to remove unbound coating antibody. T cells were seeded at 1∴105 cells per well and incubated with T2 cells alone, T2 cells pulsed with a PSGR peptide (5 µg/mL) or an irrelevant peptide as a negative control. Cells stimulated with 5 µg/mL OKT3 antibody (Ortho Biotech; Bridgewater, N.J., USA) were used as positive control. After incubating samples for 18-20 hrs at 37° C. and 5% CO2, plates were washed with wash solution. 0.75 µg/mL Biotinylated anti-human IFN-γ (Pierce Biotechnology; Rockford, Ill., USA) was added, and plates were incubated for 2 hrs at room temperature. After incubation, plates were washed with wash solution and incubated further with Poly-HRP-Streptavidin (Thermo Fisher Scientific; Rochester, N.Y., USA) diluted 1:1000 in PBS/1% BSA for 1 hr. Plates were washed and 200 µL of 4-chloro-1-naphthol substrate (Sigma-Aldrich Co.; St. Louis, Mo., USA) was added to each well. Finally, plates were washed under running tap water and dried at room temperature. IFN-γ spot-forming cells (SFC) were enumerated using an ELISPOT reader (C.T.L. Technologies, Minneapolis, Minn., USA).

RNA Extraction and RT-PCR

RNA extraction and RT-PCR was carried out as reported previously [30]. In brief, total RNA was extracted from prostate cancer cells with 1 mL Trizol reagent (Invitrogen; Carlsbad, Calif., USA). Three micrograms of RNA was reverse-transcribed to cDNA in 30 μl volume and 1 μl of each cDNA was used in subsequent PCR reaction with a pair of PSGR specific primers: Primer 1: 5'-GAAGATCTAT-GAGTTCCTGCAACTTC-3' (SEQ ID NO: 22), primer 2: 5'-CCCAAGCTT TCACTTGCCTCCCACAG-3' (SEQ ID NO: 23). β-actin was used as loading control: primer 1: 5'-CATGATGGAGTTGAAGGTAGTTTCG-3' (SEQ ID NO: 24); Primer 2: 5'-CAGACTATGCTGTCCCTG-TACGC-3' (SEQ ID NO: 25). The PCR reaction was carried out under the following conditions: 94° C. for 2 min, 94° C. for 30 s, 56° C. for 30 s, 72° C. for 1 min 20 s, total 35 cycles, 72° C. for 10 min, and β-actin was run for 25 cycles. Equal amounts of PCR products were then loaded and detected by gel electrophoresis.

Cytotoxicity Assay

PSGR derived peptide-specific T cells were tested for cytotoxicity against both PC3 and LNCaP by a lactate dehydrogenase (LDH) assay (Promega; Madison, Wis., USA). The assay was performed in accordance with the manufacturer's instructions. LDH release was calculated based on the following formula:

Cytotoxicity (%)=(Experimental−Effector Spontaneous−Target Spontaneous LDH release)/(Target Maximum−Target Spontaneous LDH release)×100.

Spontaneous release was determined by using the supernatant of the target cells alone or effector cells alone, and the maximum release was determined by using the supernatant of target cells incubated with a lysis solution included in LDH kit. To determine if T cell recognition is HLA-I restricted, anti-HLA-I, anti-HLA-II, or anti-CD19 mAb (all from ATCC, Manassas, Va., USA) were added into wells at the initiation of the culture.

Intracellular IFN-γ Cytokine Staining

PSGR-derived peptide specific T cells (0.5-1×10⁶) were cultured with 0.5×10⁶ T2 cells pulsed with or without peptide (5 μg/mL) in the presence of GolgiStop (BD Pharmingen, San Diego, Calif., USA) in a 48-well plate for 4 hrs at 37° C. Cells were stained with anti-CD8 and anti-IFN-γ and analyzed using a FACScalibur machine.

Statistics

Student's t-test was used to analyze quantitative differences between the experimental wells and controls in ELISA and ELISPOT assays. $P<0.05$ was considered significant.

Results

Induction of PSGR Derived Peptide-Specific CTLs in Healthy Donors

To determine whether PSGR-reactive T cell precursors are present in healthy subjects, we obtained PBMCs from 10 HLA-A2+ healthy donors and stimulated them in vitro with each of the 21 PSGR-derived peptides containing HLA-A2-binding motif (Table 1). After 2 weeks of peptide stimulation, supernatants from peptide-stimulated T cells were analyzed by ELISA assay to detect IFN-γ release in response to T2 cells pulsed with or without corresponding peptides. As shown in Table 2, 13 PSGR-derived peptides were capable of inducing peptide-specific T-cell responses in at least one of 10 healthy subjects. Importantly, PSGR3, PSGR4 and PSGR14 could induce T cell responses in 7 out of 10 healthy subjects, indicating that these 3 peptides are immunogenic and potentially capable of expanding antigen-specific T cells in healthy subjects.

TABLE 2

Induction of peptide-specific T cells from the PBMCs of ten HLA-A2⁺ healthy subjects

|  | #1 | #2 | #3 | #4 | #5 | #6 | #7 | #8 | #9 | #10 |
|---|---|---|---|---|---|---|---|---|---|---|
| PSGR1 | 195 | 0 | 0 | 0 | 0 | 281 | — | — | — | — |
| PSGR2 | 0 | 0 | 455 | 0 | 0 | 0 | — | — | — | — |
| PSGR3 | 127 | 398 | 393 | 768 | 227 | 183 | 645 | 0 | 394 | 0 |
| PSGR4 | 302 | 152 | 457 | 0 | 407 | 226 | 847 | 0 | 0 | 459 |
| PSGR5 | 0 | 0 | 0 | 0 | 0 | 0 | — | — | — | — |
| PSGR7 | 0 | 0 | 0 | 0 | 168 | 0 | — | — | — | — |
| PSGR10 | 917 | 0 | 0 | 0 | 0 | 0 | — | — | — | — |
| PSGR11 | 0 | 0 | 0 | 0 | 0 | 0 | — | — | — | — |
| PSGR12 | 0 | 139 | 0 | 246 | 0 | 432 | — | — | — | — |
| PSGR13 | 0 | 0 | 0 | 0 | 0 | 0 | — | — | — | — |
| PSGR14 | 471 | 0 | 115 | 0 | 124 | 296 | 843 | 0 | 346 | 854 |
| PSGR15 | 0 | 0 | 456 | 0 | 0 | 0 | — | — | — | — |
| PSGR16 | 602 | 0 | 0 | 0 | 163 | 0 | — | — | — | — |
| PSGR17 | 0 | 0 | 0 | 0 | 0 | 0 | — | — | — | — |
| PSGR18 | 176 | 0 | 0 | 0 | 0 | 0 | — | — | — | — |
| PSGR19 | 0 | 0 | 0 | 0 | 195 | 0 | — | — | — | — |
| PSGR20 | 0 | 0 | 0 | 0 | 0 | 0 | — | — | — | — |
| PSGR21 | 0 | 291 | 0 | 0 | 300 | 377 | — | — | — | — |
| PSGR22 | 289 | 0 | 0 | 0 | 0 | 0 | — | — | — | — |
| PSGR23 | 0 | 0 | 0 | 0 | 0 | 0 | — | — | — | — |
| PSGR24 | 0 | 0 | 0 | 0 | 0 | 0 | — | — | — | — |

Note:
Values denote concentrations of IFN-γ (pg/ml) in the supernatants; —, not done.

TABLE 3

Induction of peptide-specific T cells from
PBMCs of HLA-A2+ prostate cancer patients

|  | #2 | #3 | #12 | #13 | #14 | #15 | #16 | #17 | #22 | #25 |
|---|---|---|---|---|---|---|---|---|---|---|
| PSGR3 | 525 | 503 | 326 | 217 | 0 | 282 | 35 | 156 | 103 | 22 |
| PSGR4 | 451 | 351 | 0 | 301 | 309 | 70 | 6.7 | 102 | 56 | 27 |
| PSGR14 | 344 | 116 | 272 | 23 | 0 | 24 | 0 | 100 | 8 | 11 |

Note:
Values denote concentrations of IFN-γ (pg/ml) in the supernatants.

Presence of PSGR-Derived Peptide Specific CTLs in Prostate Cancer Patients

Since peptide-specific T cells against PSGR3, PSGR4 and PSGR14 were found in more than 70% of healthy subjects, we reasoned that CTL precursors that recognize these 3 peptides may also be high in PBMCs of prostate cancer patients. To test our hypothesis, we examined whether these three peptide candidates can induce peptide-specific CTLs from the PBMCs of HLA-A2+ prostate cancer patients. PBMCs from prostate cancer patients were collected and stimulated in vitro with PSGR3, PSGR4 or PSGR14 peptides. As shown in Table 3, PSGR3, PSGR4 and PSGR14 indeed induced peptide-specific CTLs from PBMCs of prostate cancer patients.

Recognition of Prostate Cancer Cells by PSGR Derived Peptide-Specific T Cells

To obtain a large number of PSGR peptide-specific T cells for further analysis, we expanded PSGR peptide-specific T cells identified in Tables 2 and 3. To determine an effective concentration of peptide for loading T2 cells for T cell recognition, we performed peptide titration experiments. As shown in FIG. 1A, for all 3 peptides a peptide concentration of 5 μg/ml was sufficient to saturate the binding sites of HLA-A2 molecules on T2 cells for T cell recognition. Therefore, we consistently used this peptide concentration for pre-loading T2 cells in ELISA and/or ELISPOT assays. The expanded T cells maintained antigen-specificity and secreted significant amounts of IFN-γ after stimulation with T2 cells pulsed with the corresponding peptides, but not with a control peptide (FIGS. 1A, B, C, D). ELISPOT assay further confirmed the presence of PSGR peptide-specific T cells in expanded T cells (FIGS. 1E, F, G).

Figure 2:
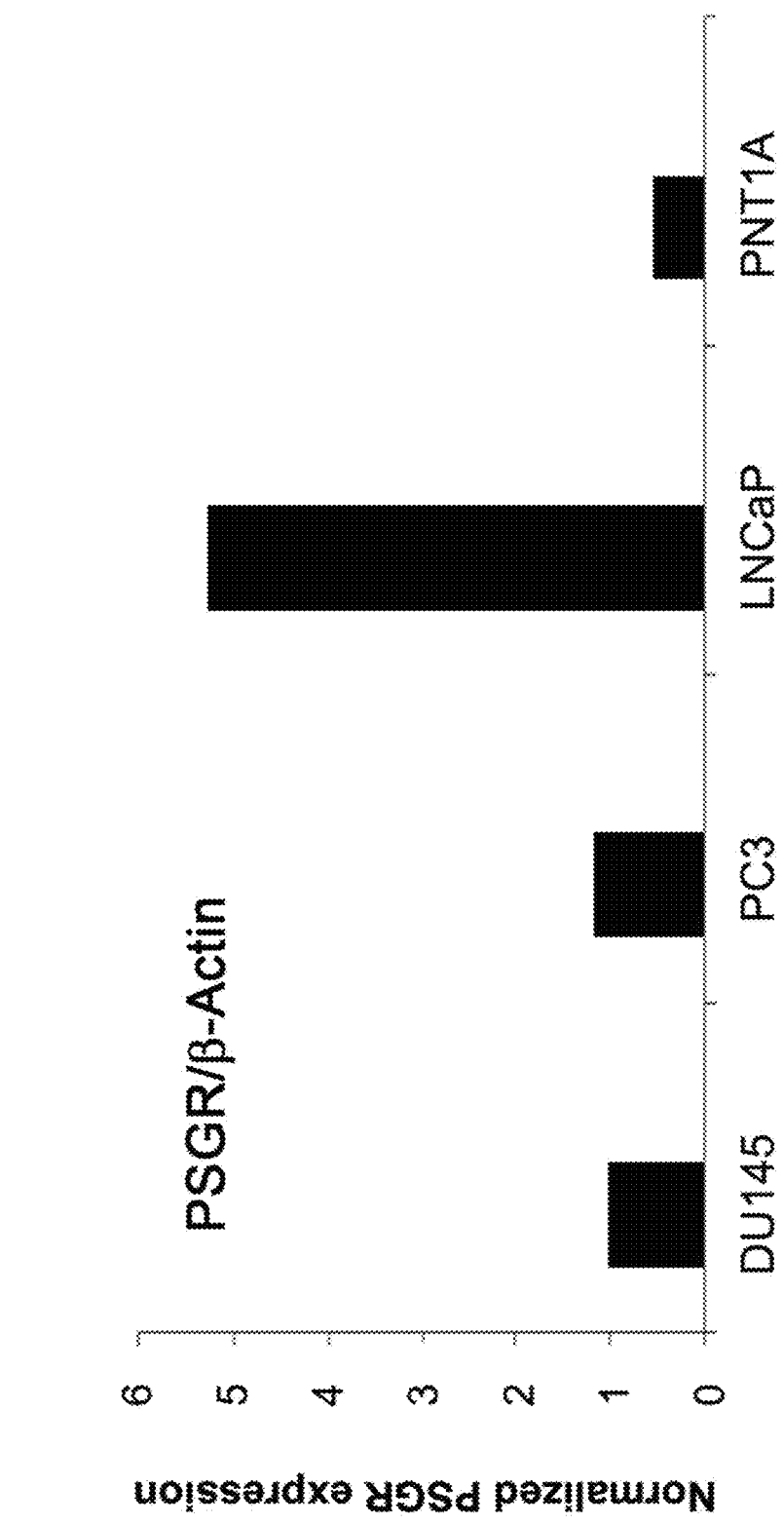
FIG. 2 shows that T cells that are specific to PSGR-derived peptides recognized HLA-A2 positive PSGR-expressing LNCaP prostate cancer cells. The expression of PSGR mRNA in different cell lines was determined by RT-PCR (A). PSGR derived peptide-specific T cells were tested for cytotoxicity against both PC3 and LNCaP by the LDH assay (B). Data from B are plotted as means±SD. Results are representative of three independent experiments. *P<0.05, versus control.
Figure 2:
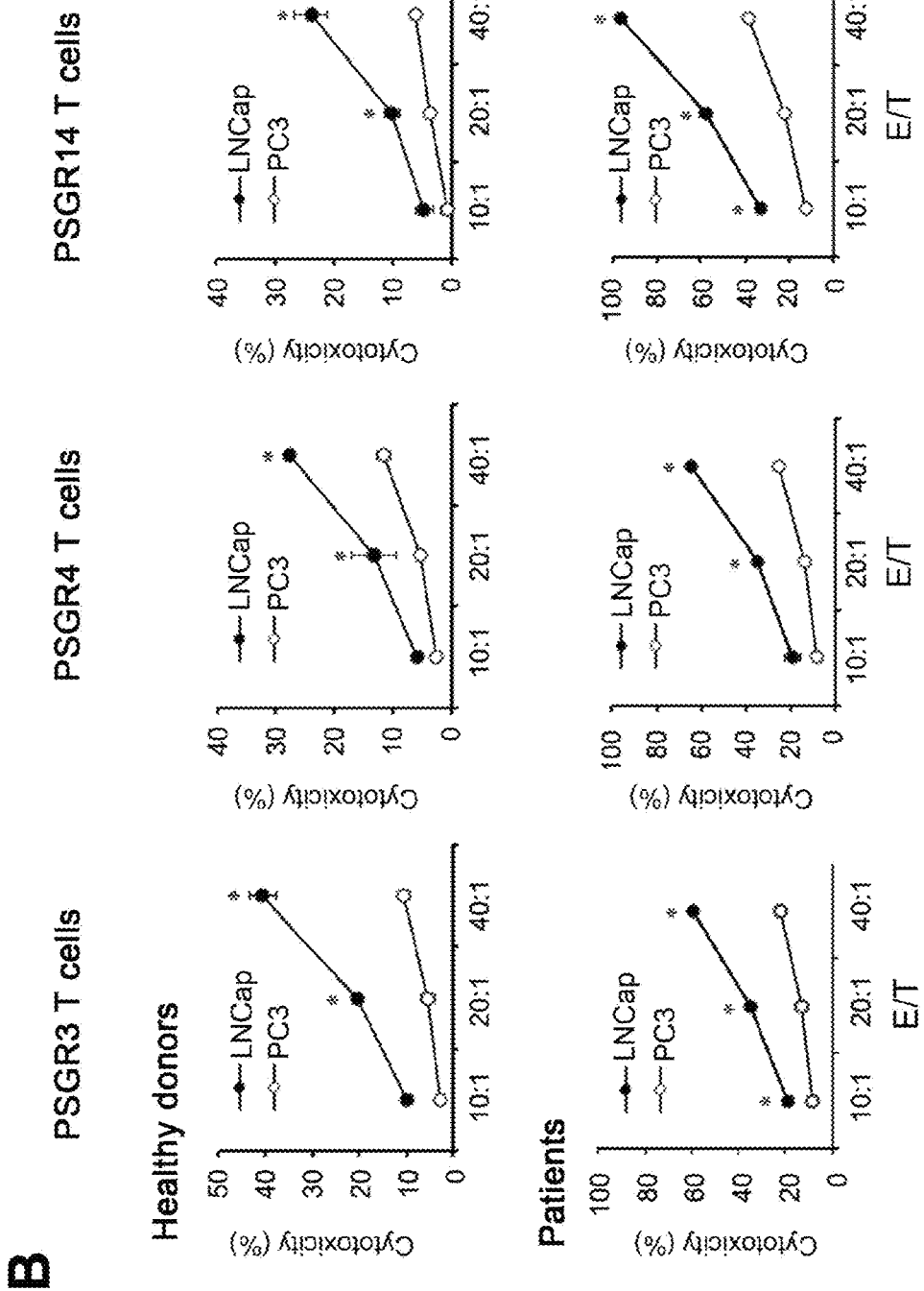

To determine whether PSGR-derived peptide-specific T cells were able to recognize and kill HLA-A2+, PSGR-expressing prostate cancer cells, we used an HLA-A2 negative PC3 cell line and an HLA-A2 positive LNCaP prostate cancer cell line. The expression of PSGR in these two cell lines was examined by RT-PCR. Consistent with a previous report [31], PSGR was highly expressed in LNCaP, but not in PC3, DU145 or a normal prostate cell line PNT1A (FIG. 2 A). As shown in FIG. 2B, PSGR3-, PSGR4-, or PSGR14-specific T cells from both healthy donors and patients could recognize and kill HLA-A2 positive, PSGR expressing LNCaP, but not HLA-A2 negative PC3 cells. These results suggest that PSGR-specific T cells recognize T cell epitopes that are endogenously processed and presented by prostate tumor cells.

T Cells Recognize PSGR-Derived Peptides in an HLA-I Restricted Manner

To test whether the responses induced by PSGR-derived peptides are dependent on CD8+ T cells, we co-cultured PSGR-derived peptide-specific T cells with T2 cells pulsed with or without corresponding peptides in the presence of GolgiStop for 4 h. Staining for CD8 molecules and intracellular IFN-γ was subsequently performed. Only CD8+ T cells were found to produce IFN-γ in response to T2 cells pulsed with corresponding peptides (FIG. 3A), while CD4+ T cells did not produce IFN-γ (data not shown).

Figure 3:
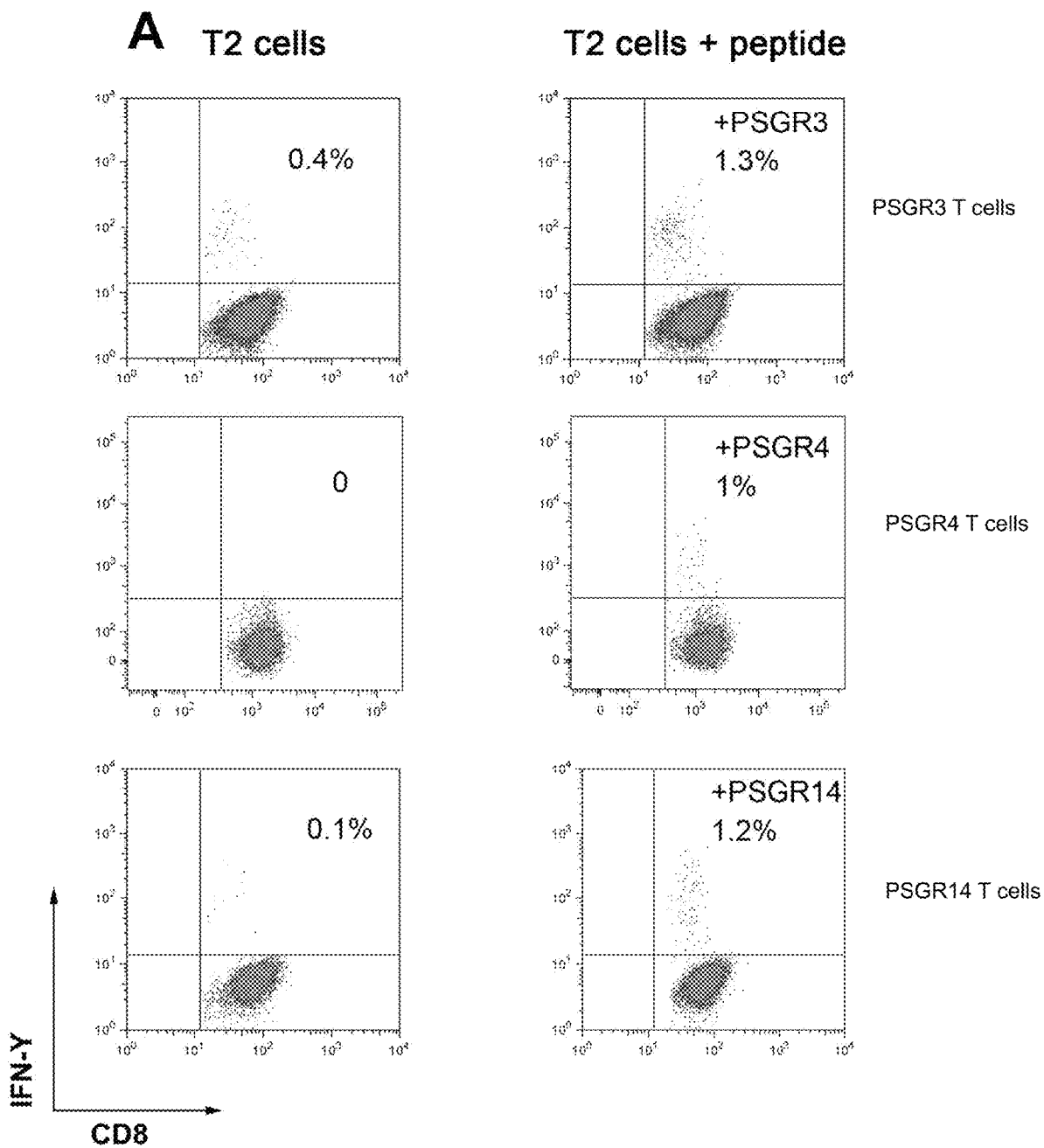
FIG. 3 shows that PSGR-derived peptide-induced T cell responses were CD8⁺ T cell dependent and restricted by HLA-I. PSGR-derived peptide-specific T cells were co-cultured with T2 cells pulsed with or without a given peptide in the presence of GolgiStop in a 48-well plate for 4 hrs at 37° C. Cells were stained with anti-CD8 and anti-IFN-γ, then analyzed on a FACScalibur machine (A). PSGR-derived peptide-specific T cells were co-incubated with LNCaP cells alone in medium, or with LNCaP cells in the presence of either anti-HLA-I mAb (W6/32), HLA-II mAb or a control mAb (anti-CD19 mAb). After 4 hours of incubation, the cytotoxicity against LNCaP was determined by the LDH assay (B). Data from B are plotted as means±SD. Results are representative of three independent experiments. *P<0.05, versus controls.
Figure 3:
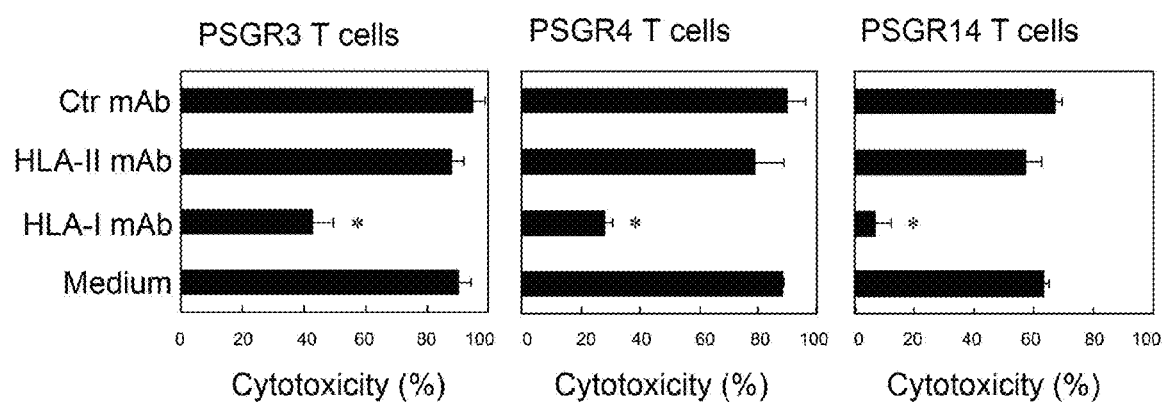

To determine whether the recognition of LNCaP cells by PSGR-derived peptide-specific T cells is HLA-I restricted, we co-cultured LNCaP cells with PSGR-derived peptide-specific T cells in the presence of either anti-HLA-I mAb (W6/32) or control mAbs (HLA-II mAb or anti-CD19 mAb). As shown in FIG. 3B, the cytotoxicity of these peptide-specific T cells was completely inhibited by the addition of anti-HLA-I mAb, but not by anti-HLA-II (HLA-DR) or a control mAb (anti-CD19), which suggests that the recognition of LNCaP cells by PSGR-derived peptide-specific T cells is HLA-I restricted.

While the present invention has been described in terms of specific embodiments, it is understood that variations and modifications will occur to those skilled in the art. Accordingly, no limitations other than those in the claims should be placed on the invention.

All documents cited in this application are hereby incorporated by reference in their entirety for their disclosure described.

REFERENCES

1. Jemal A, Bray F, Center M M, Ferlay J, Ward E, et al. (2011) Global cancer statistics. CA: a cancer journal for clinicians 61: 69-90.
2. Joniau S, Abrahamsson P A, Bellmunt J, Figdor C, Hamdy F, et al. (2012) Current vaccination strategies for prostate cancer. European urology 61: 290-306.
3. Drake C G, Antonarakis E S (2012) Current status of immunological approaches for the treatment of prostate cancer. Current opinion in urology.
4. Di Lorenzo G, Buonerba C, Kantoff P W (2011) Immunotherapy for the treatment of prostate cancer. Nature reviews Clinical oncology 8: 551-561.
5. Rosenberg S A (2011) Cell transfer immunotherapy for metastatic solid cancer—what clinicians need to know. Nature reviews Clinical oncology 8: 577-585.
6. Lesterhuis W J, Haanen J B, Punt C J (2011) Cancer immunotherapy—revisited. Nature reviews Drug discovery 10: 591-600.
7. Hodi F S, O'Day S J, McDermott D F, Weber R W, Sosman J A, et al. (2010) Improved survival with ipilimumab in patients with metastatic melanoma. The New England journal of medicine 363: 711-723.
8. Kantoff P W, Higano C S, Shore N D, Berger E R, Small E J, et al. (2010) Sipuleucel-T immunotherapy for castration-resistant prostate cancer. The New England journal of medicine 363: 411-422.
9. Schwartzentruber D J, Lawson D H, Richards J M, Conry R M, Miller D M, et al. (2011) gp100 peptide vaccine and interleukin-2 in patients with advanced melanoma. The New England journal of medicine 364: 2119-2127.
10. DuPage M, Mazumd.ar C, Schmidt L M, Cheung A F, Jacks T (2012) Expression of tumour-specific antigens underlies cancer immunoediting. Nature 482: 405-409.
11. Hildner K, Edelson B T, Purtha W E, Diamond M, Matsushita H, et al. (2008) Batf3 deficiency reveals a critical role for CD8alpha+ dendritic cells in cytotoxic T cell immunity. Science 322: 1097-1100.
12. Lundwall A, Lilja H (1987) Molecular cloning of human prostate specific antigen cDNA. FEBS letters 214: 317-322.
13. Oesterling J E (1991) Prostate specific antigen: a critical assessment of the most useful tumor marker for adenocarcinoma of the prostate. The Journal of urology 145: 907-923.
14. Xu J, Kalos M, Stolk J A, Zasloff E J, Zhang X, et al. (2001) Identification and characterization of prostein, a novel prostate-specific protein. Cancer research 61: 1563-1568.
15. Kalos M, Askaa J, Hylander B E Repasky E A, Cai F, et al. (2004) Prostein expression is highly restricted to normal and malignant prostate tissues. The Prostate 60: 246-256.
16. Gu Z, Thomas G, Yamashiro J, Shintaku I P, Dorey F, et al. (2000) Prostate stem cell antigen (PSCA) expression increases with high gleason score, advanced stage and bone metastasis in prostate cancer. Oncogene 19: 1288-1296.
17. Kawakami M. Nakayama J (1997) Enhanced expression of prostate-specific membrane antigen gene in prostate cancer as revealed by in situ hybridization. Cancer research 57: 2321-2324.
18. Su S L, Huang I P, Fair W R, Powell C T, Heston W D (1995) Alternatively spliced variants of prostate-specific membrane antigen RNA: ratio of expression as a potential measurement of progression. Cancer research 55: 1441-1443.
19. Israeli R S, Powell C T, Fair W R, Heston W D (1993) Molecular cloning of a complementary DNA encoding a prostate-specific membrane antigen. Cancer research 53: 227-230.
20. Solin T, Kontturi M, Pohlmann R, Vihko P (1990) Gene expression and prostate specificity of human prostatic acid phosphatase (PAP): evaluation by RNA blot analyses. Biochimica et biophysics acta 1048: 72-77.
21. Tsavaler L, Shapero M H, Morkowski S. Laus R (2001) Trp-p8, a novel prostate-specific gene, is up-regulated in prostate cancer and other malignancies and shares high homology with transient receptor potential calcium channel proteins. Cancer research 61: 3760-3769.
22. Kiessling A, Fussel S, Wehner R, Bachmann M, Wirth M P, et al. (2008) Advances in specific immunotherapy for prostate cancer. European urology 53: 694-708.
23. Xu L L, Stackhouse B G, Florence K, Zhang W, Shanmugam N, et al. (2000) PSGR, a novel prostate-specific gene with homology to a G protein-coupled receptor, is overexpressed in prostate cancer. Cancer research 60: 6568-6572.
24. Yuan T T, Toy P, McClary J A, Lin R J, Miyamoto N G, et al. (2001) Cloning and genetic characterization of an evolutionarily conserved human olfactory receptor that is differentially expressed across species. Gene 278: 41-51.
25. Weng J, Wang J, Cai Y, Stafford U, Mitchell D, et al. (2005) Increased expression of prostate-specific G-protein-coupled receptor in human prostate intraepithelial neoplasia and prostate cancers. International journal of cancer Journal international du cancer 113: 811-818.
26. Hammond A S, Klein M R, Corrah T, Fox A, Jaye A, et al. (2005) Mycobacterium tuberculosis genome-wide screen exposes multiple CD8 T cell epitopes. Clinical and experimental immunology 140: 109-116.
27. Wang M, Lamberth K, Harndahl M, Roder G, Stryhn A, et al. (2007) CTL epitopes for influenza A including the H5N1 bird flu; genome-, pathogen-, and HLA-wide screening. Vaccine 25: 2823-2831.
28. Zeng G, Wang X. Robbins P F, Rosenberg S A, Wang R F (2001) CD4(+) T cell recognition of MHC class II-restricted epitopes from NY-ESO-1 presented by a prevalent HLA DP4 allele: association with NY-ESO-1 antibody production. Proceedings of the National Academy of Sciences of the United States of America 98: 3964-3969.
29. Dudley M E, Wunderlich J R, Shelton T E, Even J, Rosenberg S A (2003) Generation of tumor-infiltrating lymphocyte cultures for use in adoptive transfer therapy for melanoma patients. Journal of immunotherapy 26: 332-342.
30. Weng J, Ma W, Mitchell D, Zhang J, Liu M (2005) Regulation of human prostate-specific G-protein coupled receptor, PSGR, by two distinct promoters and growth factors. Journal of cellular biochemistry 96: 1034-1048.
31. Carlsson B, Forsberg O, Bengtsson M, Totterman T H, Essand M (2007) Characterization of human prostate and breast cancer cell lines for experimental T cell-based immunotherapy. The Prostate 67: 389-395.
32. Van den Eynde B J, Boon T (1997) Tumor antigens recognized by T lymphocytes. International journal of clinical & laboratory research 27: 81-86.
33. Boon T, Cerottini J C, Van den Eynde B, van der Bruggen P, Van Pel A (1994) Tumor antigens recognized by T lymphocytes. Annual review of immunology 12: 337-365.
34. Novellino L, Castelli C, Panniani G (2005) A listing of human tumor antigens recognized by T cells: March 2004 update. Cancer immunology, immunotherapy: CII 54: 187-207.
35. Cormier J N, Hijazi Y M, Abati A, Fetsch P, Bettinotti M, et al. (1998) Heterogeneous expression of melanoma-associated antigens and HLA-A2 in metastatic melanoma in vivo. International journal of cancer Journal international du cancer 75: 517-524.
36. Albino A P, Lloyd K O, Houghton A N, Oettgen H F, Old L J (1981) Heterogeneity in surface antigen and glycoprotein expression of cell lines derived from different melanoma metastases of the same patient. Implications for the study of tumor antigens. The Journal of experimental medicine 154: 1764-1778.
37. Mellman I, Coukos G, Dranoff G (2011) Cancer immunotherapy comes of age. Nature 480: 480-489.

What is claimed is:

1. A method of inducing interferon-gamma release in T cells and inducing T cells that recognize PSGR-expressing cells in a HLA-class dependent manner in a patient in need thereof comprising administering to the patient an effective amount of a peptide selected from the group of peptides consisting of PSGR3 having the amino acid sequence of SEQ ID NO:3, PSGR4 having the amino acid sequence of SEQ ID NO: 4 and PSGR14 having the amino acid sequence of SEQ ID NO: 11, or combinations of two or more of the peptides, wherein the patient is suffering from prostate cancer, and wherein interferon-gamma release in T cells is induced and T cells that recognize PSGR-expressing cells in a HLA-class dependent manner are induced in said patient.

2. The method of claim 1 wherein the peptide is administered intradermally.

3. The method of claim 1 further comprising administering to the patient granulocyte macrophage colony stimulating factor (GM-CSF).

4. The method of claim 1 or claim 3 further comprising administering to a patient an amount effective to increase a T cell immune response: a TLR9 agonist, an inhibitor of CTLA4 or an inhibitor of PD-1.

5. The method of claim 4 wherein the inhibitor of PD-1 is a monoclonal antibody.

* * * * *

SEQUENCE LISTING

<160> NUMBER OF SEQ ID NOS: 25

<210> SEQ ID NO 1

```
<211> LENGTH: 9
<212> TYPE: PRT
<213> ORGANISM: Artificial Sequence
<220> FEATURE:
<223> OTHER INFORMATION: PSGR1

<400> SEQUENCE: 1

Val Leu Asn Pro Ile Val Tyr Gly Val
1               5

<210> SEQ ID NO 2
<211> LENGTH: 9
<212> TYPE: PRT
<213> ORGANISM: Artificial Sequence
<220> FEATURE:
<223> OTHER INFORMATION: PSGR2

<400> SEQUENCE: 2

Lys Leu Ala Cys Asp Asp Ile Arg Val
1               5

<210> SEQ ID NO 3
<211> LENGTH: 9
<212> TYPE: PRT
<213> ORGANISM: Artificial Sequence
<220> FEATURE:
<223> OTHER INFORMATION: PSGR3

<400> SEQUENCE: 3

Ile Leu Ala Asn Ile Tyr Leu Leu Val
1               5

<210> SEQ ID NO 4
<211> LENGTH: 9
<212> TYPE: PRT
<213> ORGANISM: Artificial Sequence
<220> FEATURE:
<223> OTHER INFORMATION: PSGR4

<400> SEQUENCE: 4

Trp Leu Ala Phe Pro Leu Cys Ser Leu
1               5

<210> SEQ ID NO 5
<211> LENGTH: 9
<212> TYPE: PRT
<213> ORGANISM: Artificial Sequence
<220> FEATURE:
<223> OTHER INFORMATION: PSGR5

<400> SEQUENCE: 5

Tyr Leu Leu Ile Leu Lys Thr Val Leu
1               5

<210> SEQ ID NO 6
<211> LENGTH: 9
<212> TYPE: PRT
<213> ORGANISM: Artificial Sequence
<220> FEATURE:
<223> OTHER INFORMATION: PSGR7

<400> SEQUENCE: 6

Cys Leu His Gln Asp Val Met Lys Leu
1               5

<210> SEQ ID NO 7
<211> LENGTH: 10
```

```
<212> TYPE: PRT
<213> ORGANISM: Artificial Sequence
<220> FEATURE:
<223> OTHER INFORMATION: PSGR10

<400> SEQUENCE: 7

Ser Leu Leu Ile Ser Phe Ser Tyr Leu Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: PSGR11

<400> SEQUENCE: 8

His Val Cys Ala Val Phe Ile Phe Tyr Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: PSGR12

<400> SEQUENCE: 9

Gly Leu Glu Glu Ala Gln Phe Trp Leu Ala
1               5                   10

<210> SEQ ID NO 10
<211> LENGTH: 10
<212> TYPE: PRT
<213> ORGANISM: Artificial Sequence
<220> FEATURE:
<223> OTHER INFORMATION: PSGR13

<400> SEQUENCE: 10

Ala Leu Met Ala Pro Leu Pro Val Phe Ile
1               5                   10

<210> SEQ ID NO 11
<211> LENGTH: 10
<212> TYPE: PRT
<213> ORGANISM: Artificial Sequence
<220> FEATURE:
<223> OTHER INFORMATION: PSGR14

<400> SEQUENCE: 11

Val Ile Leu Ala Asn Ile Tyr Leu Leu Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: PSGR15

<400> SEQUENCE: 12

Leu Leu Ile Leu Lys Thr Val Leu Gly Leu
1               5                   10

<210> SEQ ID NO 13
<211> LENGTH: 10
<212> TYPE: PRT
```

```
<213> ORGANISM: Artificial Sequence
<220> FEATURE:
<223> OTHER INFORMATION: PSGR16

<400> SEQUENCE: 13

Tyr Leu Ile Ala Val Leu Gly Asn Leu Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: PSGR17

<400> SEQUENCE: 14

Cys Met Leu Ser Gly Ile Asp Ile Leu Ile
1               5                   10

<210> SEQ ID NO 15
<211> LENGTH: 10
<212> TYPE: PRT
<213> ORGANISM: Artificial Sequence
<220> FEATURE:
<223> OTHER INFORMATION: PSGR18

<400> SEQUENCE: 15

Leu Leu Gln Met Phe Ala Ile His Ser Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: PSGR19

<400> SEQUENCE: 16

Ser Leu His Glu Pro Met Tyr Ile Phe Leu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: PSGR20

<400> SEQUENCE: 17

Leu Leu Ala Met Ala Phe Asp Arg Tyr Val
1               5                   10

<210> SEQ ID NO 18
<211> LENGTH: 10
<212> TYPE: PRT
<213> ORGANISM: Artificial Sequence
<220> FEATURE:
<223> OTHER INFORMATION: PSGR21

<400> SEQUENCE: 18

Val Leu Gly Asn Leu Thr Ile Ile Tyr Ile
1               5                   10

<210> SEQ ID NO 19
<211> LENGTH: 10
<212> TYPE: PRT
<213> ORGANISM: Artificial Sequence
```

```
<220> FEATURE:
<223> OTHER INFORMATION: PSGR22

<400> SEQUENCE: 19

Phe Ile Phe Tyr Val Pro Phe Ile Gly Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: PSGR23

<400> SEQUENCE: 20

Thr Leu Pro Arg Val Thr Lys Ile Gly Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: PSGR24

<400> SEQUENCE: 21

Tyr Val Pro Phe Ile Gly Leu Ser Met Val
1               5                   10

<210> SEQ ID NO 22
<211> LENGTH: 26
<212> TYPE: PRT
<213> ORGANISM: Artificial Sequence
<220> FEATURE:
<223> OTHER INFORMATION: Primer 1

<400> SEQUENCE: 22

Gly Ala Ala Gly Ala Thr Cys Thr Ala Thr Gly Ala Gly Thr Thr Cys
1               5                   10                  15

Cys Thr Gly Cys Ala Ala Cys Thr Thr Cys
                20                  25

<210> SEQ ID NO 23
<211> LENGTH: 26
<212> TYPE: PRT
<213> ORGANISM: Artificial Sequence
<220> FEATURE:
<223> OTHER INFORMATION: Primer 2

<400> SEQUENCE: 23

Cys Cys Cys Ala Ala Gly Cys Thr Thr Thr Cys Ala Cys Thr Thr Gly
1               5                   10                  15

Cys Cys Thr Cys Cys Cys Ala Cys Ala Gly
                20                  25

<210> SEQ ID NO 24
<211> LENGTH: 25
<212> TYPE: PRT
<213> ORGANISM: Artificial Sequence
<220> FEATURE:
<223> OTHER INFORMATION: Primer 1

<400> SEQUENCE: 24

Cys Ala Thr Gly Ala Thr Gly Gly Ala Gly Thr Thr Gly Ala Ala Gly
1               5                   10                  15
```

```
Gly Thr Ala Gly Thr Thr Thr Cys Gly
            20                  25

<210> SEQ ID NO 25
<211> LENGTH: 23
<212> TYPE: PRT
<213> ORGANISM: Artificial Sequence
<220> FEATURE:
<223> OTHER INFORMATION: Primer 2

<400> SEQUENCE: 25

Cys Ala Gly Ala Cys Thr Ala Thr Gly Cys Thr Gly Thr Cys Cys Cys
1               5                   10                  15

Thr Gly Thr Ala Cys Gly Cys
            20
```